US00PP36931P2

(12) United States Plant Patent
Ammerlaan

(10) Patent No.: US PP36,931 P2
(45) Date of Patent: Sep. 2, 2025

(54) ***CRASSULA* PLANT NAMED 'OVWOODS06'**

(50) Latin Name: ***Crassula ovata* (Mill.) Druce**
Varietal Denomination: OVWOODS06

(71) Applicant: Ovata B.V., Bleiswijk (NL)

(72) Inventor: Johannes Hendrikus Adrianus Ammerlaan, Bleiswijk (NL)

(73) Assignee: Ovata B.V., Bleiswijk (NL)

( * ) Notice: Subject to any disclaimer, the term of this patent is extended or adjusted under 35 U.S.C. 154(b) by 0 days.

(21) Appl. No.: 18/831,477

(22) Filed: Feb. 7, 2025

(51) Int. Cl.
*A01H 5/00* (2018.01)
*A01H 6/32* (2018.01)

(52) U.S. Cl.
USPC ..... Plt./373

(58) Field of Classification Search
USPC ..... Plt./373
See application file for complete search history.

(56) References Cited

U.S. PATENT DOCUMENTS

PP28,426 P3 * 9/2017 Ammerlaan ..... Plt./373

* cited by examiner

*Primary Examiner* — Karen M Redden
(74) *Attorney, Agent, or Firm* — Samuel R. McCoy, Jr.

(57) ABSTRACT

A new and distinct *Crassula* plant named 'OVWOODS06' which is characterized by the combination of a compact and freely-branching growth habit, an abundance of obovate to elliptic foliage with an upright attitude, dark green and heavily glaucous foliage with dark greyed-purple to brown margins, and the stability of all characteristics from generation to generation.

2 Drawing Sheets

Latin name of the genus and species: The Latin name of the genus and species of the novel variety disclosed herein is *Crassula ovata* (Mill.) Druce.

Variety denomination: The inventive variety of *Crassula* disclosed herein has been given the variety denomination 'OVWOODS06'.

BACKGROUND OF THE INVENTION

Parentage: 'OVWOODS06' originated as a naturally occurring, whole-plant mutation of *Crassula* 'Minova Magic' (Community Plant Variety Rights grant number 37,471), a variety developed and owned by the inventor. The inventor of 'OVWOODS06' is a commercial ornamental plant producer who regularly discovers mutations of *Crassula* at his greenhouse operation in Bleiswijk, The Netherlands. For said mutations which seem to exhibit commercial potential, cuttings are taken and rooted to produce trial plants which are subsequently grown for evaluation. The variety now called 'OVWOODS06', which was initially discovered in December of 2018 as a whole-plant mutation of 'Minova Magic', exhibited a compact growth habit with dark green, glaucous foliage held upright. At the time of discovery, cuttings were taken, and the resulting plants were evaluated at the inventor's greenhouse. After further evaluation, it was determined that the candidate's foliage characteristics would prove favorable for commercial marketability. The new variety was given the variety denomination 'OVWOODS06'.

Asexual Reproduction: 'OVWOODS06' was first asexually reproduced in December 2018 in a commercial greenhouse in Bleiswijk, The Netherlands by way of meristematic tissue culture. and has since been vegetatively propagated through four additional generations. Through four subsequent generations, the unique features of this cultivar have proven to be stable and true to type.

SUMMARY OF THE INVENTION

The cultivar 'OVWOODS06' has not been observed under all possible environmental conditions and the phenotype may vary somewhat with variations in environment such as temperature, day length, and light intensity, without, however, any variance in genotype. The following traits have been repeatedly observed and are determined to be the unique characteristics of 'OVWOODS06'. These characteristics in combination distinguish 'OVWOODS06' as a new and distinct *Crassula* cultivar:

1. *Crassula* 'OVWOODS06' exhibits a compact and freely-branching growth habit; and
2. *Crassula* 'OVWOODS06' exhibits relative abundance of obovate to elliptic foliage with an upright attitude; and
3. *Crassula* 'OVWOODS06' exhibits dark green, heavily glaucous foliage that is margined with dark greyed-purple to brown.

BOTANICAL DESCRIPTION OF THE PLANT

Figure 1:
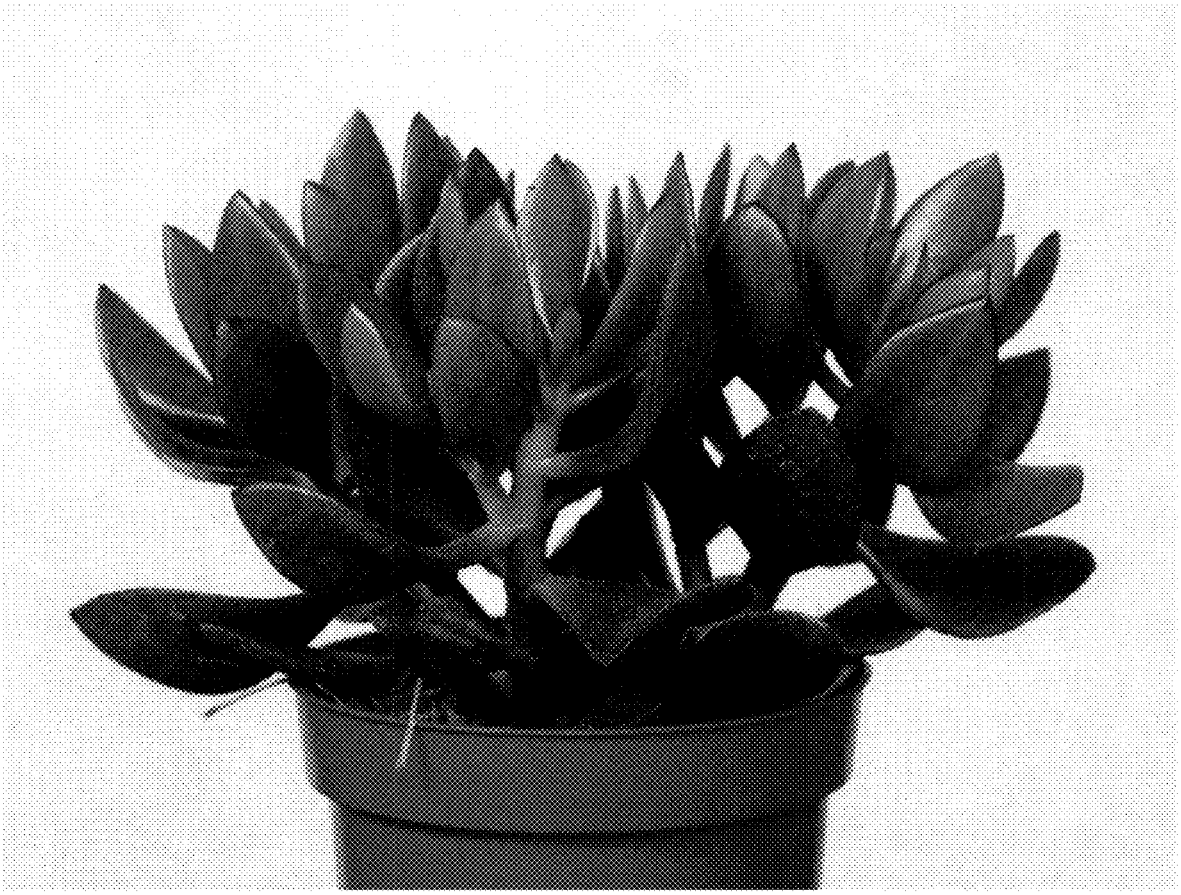
FIG. 1 illustrates, as nearly true as it is reasonably possible to make the same in color photographs of this type, an exemplary plant of 'OVWOODS06' grown in a commercial greenhouse in Heerhugowaard, The Netherlands. This plant is approximately 2 years old, shown planted in a 12 cm container.
Figure 2:
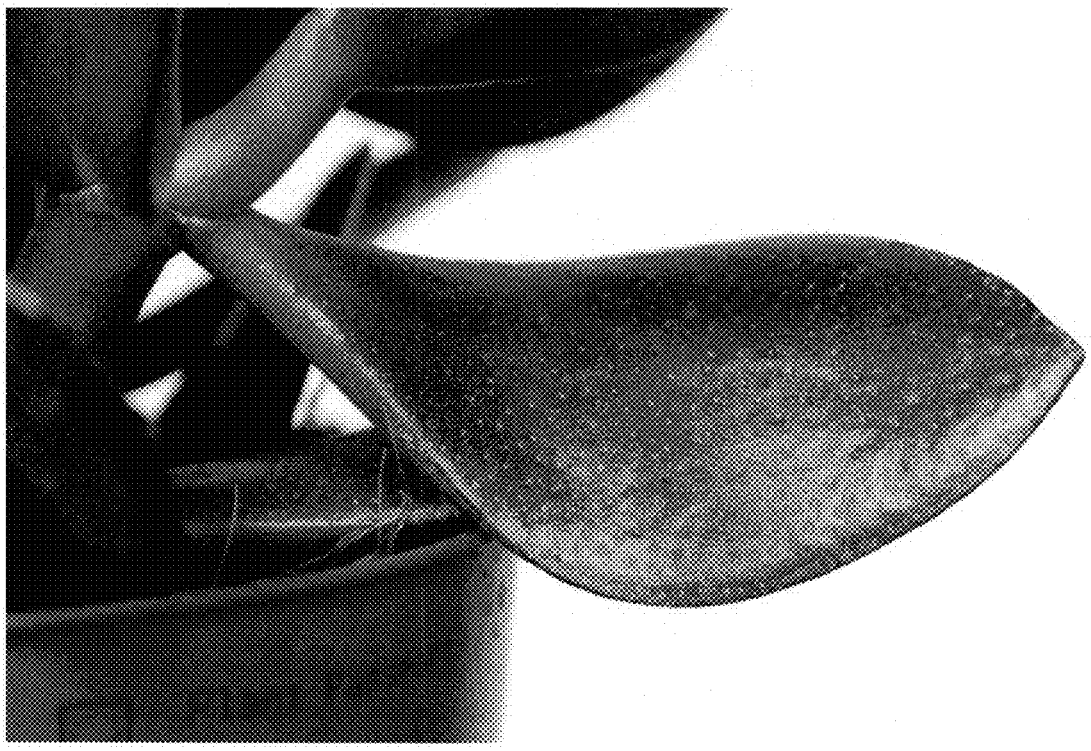
FIG. 2 illustrates, as nearly true as it is reasonably possible to make the same in color photographs of this type, the typical foliage of 'OVWOODS06'.

The following observations and measurements made in November of 2020 describe averages from a sample set of six specimens of 2-year-old 'OVWOODS06' plants grown in 12 cm nursery containers at commercial greenhouse in Bleiswijk, The Netherlands. The plants were grown in full sun to semi-shade. Plants were maintained with a standard fertilization program for plants of this type and no chemical pest measures. and regularly watered with overhead irrigation as well as through use of ebb-and-flow hydroponic greenhouse benches. No chemical pest measures were taken.

Those skilled in the art will appreciate that certain characteristics will vary with older or, conversely, with younger plants. 'OVWOODS06' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climactic and cultural conditions. Color notations are based on *The Royal Horticultural Society Colour Chart*, The Royal Horticultural Society, London, Sixth Edition.

A botanical description of 'OVWOODS06' and comparisons with the parent and closest known commercial comparator are provided below.

Plant description:

*Growth habit*.—Broad spreading to upright perennial.

*Plant form*.—Irregular flattened globular to globular.

*Average height*.—12.4 cm from the soil level to the top of the foliar plane.

*Plant spread*.—Average of 19.3 cm.

*Growth rate*.—Slow to moderately fast growing.

*Plant vigor*.—Moderately vigorous.

*Propagation type*.—Stem cuttings.

*Time to initiate roots*.—Approximately 14 days to initiate roots at temperatures ranging from 15 to 20 degrees Celsius.

*Time to produce a rooted cutting*.—Approximately 6 weeks to produce a rooted cutting.

*Disease resistance*.—Neither resistance nor susceptibility to typical *Crassula* pests and diseases has been observed.

*Environmental tolerances*.—Adapt to, at least, USDA Zones 10 and 13 and temperatures as high as 40 degrees Celsius; low tolerance to rain; moderate to high tolerance to wind.

Root system:

*General*.—Moderately dense and freely branched rooting; roots are moderately fibrous.

*Distribution in the soil profile*.—Shallow to moderately deep.

*Diameter of roots*.—0.5 mm on average.

*Texture*.—Smooth and glabrous.

*Color*.—Greyed-orange, nearest to RHS 165C.

Stem:

*General branching habit*.—A main stem, freely branching with lateral branches. Pinching isn't required but will improve branching.

*Main stems*.—Quantity of main stems per plant — 3. Attitude — Upright. Cross-section — Rounded. Texture — Glabrous; glaucous. Luster — Slightly glossy, due to the epicuticular wax. Strength — Strong. Color, juvenile — Yellow-green, nearest to RHS 144B. Color, mature — Green, nearest to in between RHS 138A and 143B; epicuticular wax colored greyed-green, nearest to RHS 198C and 198D. Color at internodes — Green, nearest to a blend of RHS 138A and 143B. Color of the oldest wood — Green, nearest to RHS 138A; epicuticular wax is colored greyed-orange, nearest to RHS 165D.

*Lateral branches*.—Quantity of lateral branches — 10. Length of lateral branches — Approximately 4.1 cm. Diameter of lateral branches — Approximately 0.7 cm. Internode length — Approximately 1.4 cm. Attitude — At an average angle of 45 degrees to the main stem. Cross-section — Rounded. Texture — Glabrous; glaucous. Luster — Matte. Strength — Strong. Color, juvenile — Yellow-green, nearest to RHS 144B. Color, mature — Green, nearest to in between RHS 138A and 143B; epicuticular wax colored greyed-green, nearest to RHS 198C and 198D. Color at internodes — Green, nearest to a blend of RHS 138A and 143B.

Foliage:

*Phyllotaxy*.—Decussate.

*Division*.—Simple.

*Attachment*.—Sessile.

*Quantity*.—6.

*Attitude*.—Upward.

*Lamina*.—Shape — Obovate to elliptic. Aspect — Longitudinally convex; slightly to moderately curled upward, distally. Dimensions — 6.5 cm long and 2.9 cm wide. Thickness — Approximately 0.6 cm. Apex — Broad, bluntly acute to obtuse; occasionally shallow retuse. Base — Narrow cuneate. Margin — Entire; coarsely undulated and unlobed. Texture, adaxial surface — Smooth, glabrous, and densely and finely dotted with lenticels. Texture, abaxial surface — Smooth, glabrous, and densely and finely dotted with lenticels. Luster, adaxial surface — Matte. Luster, abaxial surface — Matte. Color — Juvenile foliage, adaxial surface — Yellow-green, nearest to RHS 144A, and slightly darker at the central portion of the lamina, nearest to RHS 143B; narrowly margined greyed-purple, nearest to RHS 187A and 187B; lenticels are greyed-green, nearest to a mixture of RHS 189C, 189D, and N189D. Juvenile foliage, abaxial surface — Green, nearest to RHS 143C; narrowly margined greyed-purple, nearest to RHS 187B; lenticels are greyed-green, nearest to a mixture of RHS 189C, 189D, and N189D. Mature foliage, adaxial surface — Green to yellow-green, nearest to a blend of RHS NN137A and 147A; narrowly margined with a mixture of greyed-purple and brown, nearest to RHS N186C and 200A; lenticels are greyed-green, nearest to RHS 189C, 189D, and N189D. Mature foliage, abaxial surface — Green to yellow-green, nearest to a blend of RHS NN137A and 147A, and slightly darker at the central portion of the lamina, nearest to RHS 137B; narrowly margined with a mixture of greyed-purple and brown, nearest to RHS N186C and 200A; lenticels are greyed-green, nearest to RHS 189C, 189D, and N189D. Venation — No veins are visible.

Inflorescence: No flowering has been observed to date.

COMPARISON WITH THE PARENT PLANT

Plants of the new cultivar 'OVWOODS06' differ from the parent, *Crassula* 'Minova Magic' (Community Plant Variety Rights grant number 37,471), in the following characteristics described in Table 1 below.

TABLE 1

| Characteristic | 'OVWOODS06' | 'Minova Magic' |
|---|---|---|
| Plant size. | Smaller and more compact than 'Minova Magic'. | Larger than 'OVWOODS06'. |
| General coloration of the foliage. | Dark green and narrowly margined with dark greyed-purple to a mixture of greyed-purple and brown. | Greyed-green with margins lightly to moderately suffused with greyed-red. |
| Foliage size and shape. | Smaller than 'Minova Magic'; narrower with a more pointed apex. | Larger than 'OVWOODS06'; broader with a more obtuse apex. |
| Foliage luster. | Matte. | Somewhat glossy. |
| Foliage attitude. | More upright than 'Minova Magic'. | More relaxed than 'OVWOODS06'. |

TABLE 2

| Characteristic | 'OVWOODS06' | 'Crasmada' |
|---|---|---|
| Plant size. | Shorter than 'Crasmada'. | Taller than 'OVWOODS06'. |
| Length of lateral branches. | Shorter than 'Crasmada'. | Longer than 'OVWOODS06'. |
| Foliage shape. | Obovate to elliptic. | Obovate. |
| Foliage size. | Longer and narrower than 'Crasmada'. | Shorter and broader than 'OVWOODS06'. |
| General coloration of the foliage. | Dark green. | |
| Lenticels coloration. | Foliage covered in greyed-orange lenticels. | Foliage covered in greyed-green lenticels. |

COMPARISON WITH THE CLOSEST KNOWN COMPARATOR

Plants of the new cultivar 'OVWOODS06' differ from the most similar variety known to the inventor, *Crassula* 'CRASMADA' (U.S. Plant Pat. No. 28,426), in the following characteristics described in Table 2 below.

That which is claimed is:

1. A new and distinct variety of *Crassula* plant named 'OVWOODS06', substantially as described and illustrated herein.

* * * * *